(12) United States Patent
Gutman et al.

(10) Patent No.: US 7,288,660 B2
(45) Date of Patent: Oct. 30, 2007

(54) PROCESS FOR PREPARING ONDANSETRON HYDROCHLORIDE DIHYDRATE HAVING A DEFINED PARTICLE SIZE

(75) Inventors: Daniella Gutman, Rishon Lezion (IL); Rosa Cyjon, Haifa (IL)

(73) Assignee: Taro Pharmaceutical Industries Limited, Haifa Bay (IL)

( * ) Notice: Subject to any disclaimer, the term of this patent is extended or adjusted under 35 U.S.C. 154(b) by 0 days.

(21) Appl. No.: 11/122,401

(22) Filed: May 5, 2005

(65) Prior Publication Data

US 2005/0261351 A1 Nov. 24, 2005

Related U.S. Application Data

(60) Provisional application No. 60/568,992, filed on May 7, 2004.

(51) Int. Cl.
*C07D 233/20* (2006.01)
(52) U.S. Cl. .................................................. 548/311.4
(58) Field of Classification Search .............. 548/311.4
See application file for complete search history.

(56) References Cited

U.S. PATENT DOCUMENTS

| | | | |
|---|---|---|---|
| 4,695,578 | A | 9/1987 | Coates et al. |
| 4,753,789 | A | 6/1988 | Tyers et al. |
| 4,826,689 | A | 5/1989 | Violanto |
| 5,118,528 | A | 6/1992 | Fessi et al. |
| 5,622,720 | A | 4/1997 | Collin |
| 6,544,550 | B1 | 4/2003 | Tyers et al. |
| 2002/0115707 | A1 | 8/2002 | Lidor-Hadas et al. |
| 2004/0019093 | A1 | 1/2004 | Aronhime et al. |
| 2004/0198794 | A1 | 10/2004 | Westheim et al. |

FOREIGN PATENT DOCUMENTS

| | | |
|---|---|---|
| EP | 90307044.9 | 3/1991 |
| GB | 2153821 B | 8/1985 |
| WO | WO 2004/035567 A1 | 4/2004 |
| WO | WO 2004/063189 A1 | 7/2004 |

OTHER PUBLICATIONS

Suzuki et al., Studies on methods of particle size reduction of medical compounds VIII. Size reduction by freeze-dying . . . Chem. Pharm Bull., 27(5):1214-1222 (1979).
Sekiguchi et al., Studies on methods of particle size reduction of medicinal compounds VI . . . Chem. Pharm. Bull. 24(7):1621-1630 (1976).
Sekiguchi et al., Studies on methods of particle size reduction of medicinal compounds II . . . Chem. Pharm. Bull. 12(10):1192-1197 (1964).
Sekiguchi et al. Studies on the methods of size recution of medicinal compounds III . . . Chem. Pharm. Bull. 16(12):2495-2502 (198).

*Primary Examiner*—James O. Wilson
*Assistant Examiner*—Ebenezer Sackey
(74) *Attorney, Agent, or Firm*—Venable LLP; Michael A. Gollin; Lars H. Genieser

(57) ABSTRACT

The invention provides a process for preparing ondansetron hydrochloride dihydrate particles in which at least about 70% of the particles have a particle size of less than 250 μm, comprising the steps of:
(a) preparing a solution comprising ondansetron hydrochloride and water; and
(b) adding the solution into a precipitation medium which comprises a water-miscible nonsolvent for ondansetron hydrochloride, while maintaining the resulting mixture at a temperature of about 40° C. or less.

26 Claims, No Drawings

PROCESS FOR PREPARING ONDANSETRON HYDROCHLORIDE DIHYDRATE HAVING A DEFINED PARTICLE SIZE

CROSS REFERENCE TO RELATED APPLICATION

This application claims the benefit under 35 U.S.C. § 119(e) of U.S. Provisional Application No. 60/568,992, filed May 7, 2004, the disclosure of which is incorporated by reference in its entirety herein.

BACKGROUND OF THE INVENTION

1. Field of the Invention

This invention relates to a process for preparing ondansetron hydrochloride dihydrate having a defined particle size. The prepared ondansetron hydrochloride dihydrate is suitable for homogeneous distribution in a tablet blend.

2. Description of Related Art

Ondansetron (1,2,3,9-tetrahydro-9-methyl-3-[(2-methyl-1H-imidazol-1-yl)methyl]-4H-carbazol-4-one) selectively blocks the serotonin 5-HT$_3$ receptor type. Ondansetron is marketed for the treatment of nausea under the tradename ZOFRAN® (GlaxoSmithKline, Research Triangle Park, N.C.). Ondansetron has the following chemical structure:

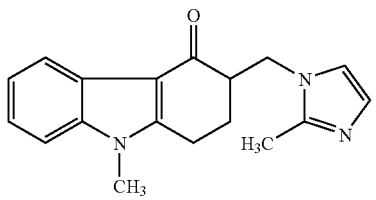

Ondansetron exists both in free base and hydrochloride dihydrate salt forms. Ondansetron hydrochloride dihydrate salt is the form used in tablet formulations. In tablet formulations, the particle size of the ondansetron hydrochloride dihydrate is critical. Because only a low dose of drug substance (i.e., ondansetron) per tablet is required, uniform tablets can only be prepared if the ondansetron hydrochloride dihydrate has a uniformly small particle size, which permits homogeneous distribution in a tablet blend (e.g., at least about 70% of the particles are smaller than 250 μm).

U.S. Pat. No. 4,695,578 ('578 patent) discloses a process for preparing ondansetron hydrochloride dihydrate having a large particle size (e.g., less than about 60% of the particles are smaller than 250 μm). The '578 patent process involves the step of cooling a solution of ondansetron hydrochloride, isopropanol, and water, optionally followed by an additional step of recrystallizing from a mixture of water and isopropanol.

A drawback of this process is that the obtained ondansetron hydrochloride dihydrate particles are too large to be homogeneously distributed in a tablet blend. Therefore, the ondansetron hydrochloride dihydrate particles described in the '578 patent cannot be used to make ondansetron hydrochloride dihydrate tablets having an acceptable uniform drug content.

As such, the particle size of the ondansetron hydrochloride dihydrate must further be reduced prior to formulation into tablets. However, conventional techniques for reducing particle size have proven to be unsuccessfull when applied to ondansetron hydrochloride dihydrate. For example, comminution milling of ondansetron hydrochloride dihydrate causes screen blockage of coarse and fine screens. Furthermore, although ondansetron hydrochloride dihydrate having a particle size of less than 250 μm can be obtained by passing the substance through a 60 mesh sieve (See UK Patent No. 2153821B), this method is not commercially viable.

U.S. Pat. No. 5,722,720 (the '720 patent) discloses a non-conventional technique for reducing particle size. In particular, the '720 patent discloses a multistep process in which ondansetron hydrochloride dihydrate is first dried at elevated temperature and reduced or atmospheric pressure, and is then cooled to ambient temperature. The process requires the heating step to be performed until the ondansetron hydrochloride dihydrate is desolvated, and requires the cooling step to be performed until the ondansetron hydrochloride is rehydrated to form ondansetron hydrochloride dihydrate.

The '720 patent process has several disadvantages. First, the '720 patent process requires a prolonged time period (i.e., 16–24 hours) for the drying/desolvating step, plus an additional prolonged time period for the cooling/rehydrating step. Second, the '720 patent process requires vigorous and carefully controlled drying conditions. For example, when the drying step is performed at 48–52° C., a reduced pressure of 100–200 torr is required. When the drying step is performed at ambient pressure, an elevated temperature of 100° C. is required.

There is a continuing need for a process for preparing ondansetron hydrochloride dihydrate having a defined particle size that is suitable for preparing ondansetron hydrochloride dihydrate tablets.

SUMMARY OF THE INVENTION

The present invention provides a process for preparing ondansetron hydrochloride dihydrate particles in which at least about 70% of the particles have a particle size of less than 250 μm, comprising the steps of:

(a) preparing a solution comprising ondansetron hydrochloride and water; and (b) adding the solution into a precipitation medium which comprises a water-miscible nonsolvent for ondansetron hydrochloride, while maintaining the resulting mixture at a temperature of about 40° C. or less.

Preferably, step (a) is performed at a temperature of about 40° C. to about 90° C. More preferably, step (a) is performed at a temperature of about 50° C. to about 80° C. More preferably, step (a) is performed at a temperature of about 65° C. to about 70° C.

Preferably, the precipitation medium has a temperature of about 30° C. or less. More preferably, the precipitation medium has a temperature of about 20° C. or less.

Preferably, step (b) is performed while maintaining the mixture at a temperature of about 30° C. or less. More preferably, step (b) is performed while maintaining the mixture at a temperature of about 20° C. or less.

Preferably, the water-miscible nonsolvent for ondansetron hydrochloride in step (b) is a $C_2$–$C_4$ alcohol. More preferably, the $C_2$–$C_4$ alcohol is isopropanol.

Preferably, step (a) is performed by mixing ondansetron with hydrochloric acid to form ondansetron hydrochloride dihydrate in a solvent system comprising water.

Preferably, the ondansetron hydrochloride in step (a) is present at a concentration of about 100 g/L to about 1,000 g/L. More preferably, the ondansetron hydrochloride in step (a) is present at a concentration of about 200 g/L to about 500 g/L.

Preferably, the solution and the precipitation medium have a vol/vol ratio of about 1:1 to about 1:10. More preferably, the solution and the precipitation medium have a vol/vol ratio of about 1:2 to about 1:5.

Optionally, the solution in step (a) may further contain a water-miscible nonsolvent for ondansetron hydrochloride. More preferably, the water-miscible nonsolvent for ondansetron hydrochloride is a $C_2$–$C_4$ alcohol. More preferably, the $C_2$–$C_4$ alcohol is isopropanol.

In accordance with the process, ondansetron hydrochloride dihydrate having a defined particle size is obtained. Preferably at least about 80% of the ondansetron hydrochloride dihydrate particles have a particle size of less than 250 µm. More preferably, at least about 90% of the ondansetron hydrochloride dihydrate particles have a particle size of less than 250 µm.

In accordance with the process, preferably at least about 30% of the ondansetron hydrochloride dihydrate particles have a particle size of greater than 60 µm. More preferably, at least about 60% of the ondansetron hydrochloride dihydrate particles have a particle size of greater than 60 µm.

In accordance with the process, preferably the ondansetron hydrochloride dihydrate particles have a mean particle size of about 25 µm to about 200 µm. More preferably, the ondansetron hydrochloride dihydrate particles have a mean particle size of about 50 µm to about 150 µm.

Preferably, ondansetron hydrochloride dihydrate particles having a defined particle size are suitable for homogeneous distribution in a tablet blend.

Preferably, the ondansetron hydrochloride dihydrate particles have a purity of at least about 99.5% (w/w). More preferably, the ondansetron hydrochloride dihydrate particles have a purity of at least about 99.8% (w/w). More preferably, the ondansetron hydrochloride dihydrate particles have a purity of at least about 99.9% (w/w).

Preferably, the ondansetron hydrochloride dihydrate particles contain about 0.05% (w/w) or less of each individual impurity. Examples of impurities include, but are not limited to, 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

Preferably, the ondansetron hydrochloride dihydrate particles contain about 0.02% (w/w) or less of 1,2,3,9-tetrahydro-9-methyl-3-methylene-4H-carbazol-4-one. Preferably, the ondansetron hydrochloride dihydrate particles contain about 0.02% (w/w) or less of 3-[(dimethylamino)methyl]-1,2,3,9-tetrahydro-9-methyl-4H-carbazol-4-one. Preferably, the ondansetron hydrochloride dihydrate particles contain about 0.02% (w/w) or less of methyl imidazole. Preferably, the ondansetron hydrochloride dihydrate particles contain about 0.02% (w/w) or less of 1,2,3,9-tetrahydro-9-methyl-4H-carbazol-4-one.

Preferably, the ondansetron hydrochloride dihydrate particles are prepared as a single batch of at least about 500 grams. More preferably, the ondansetron hydrochloride dihydrate particles are prepared as a single batch of at least about five (5) kilograms.

The present invention further provides a process for preparing ondansetron hydrochloride dihydrate particles in which at least about 70% of the particles have a particle size of less than 250 µm, comprising the steps of:

(a) preparing a solution comprising ondansetron hydrochloride and water; and
(b) adding the solution into a precipitation medium which comprises a $C_2$–$C_4$ alcohol, while maintaining the resulting mixture at a temperature of about 40° C. or less.

The present invention provides a process for preparing ondansetron hydrochloride dihydrate particles in which at least about 70% of the particles have a particle size of less than 250 µm, comprising the steps of:

(a) preparing a solution comprising ondansetron hydrochloride, water, and isopropanol; and
(b) adding the solution into a precipitation medium which comprises isopropanol, while maintaining the resulting mixture at a temperature of about 30° C. or less.

Preferably, the isopropanol and the water are present in the resulting mixture at a vol/vol ratio of about 5:1 or greater.

The present invention provides a commercial scale composition of ondansetron hydrochloride dihydrate particles having a defined a particle size.

The present invention provides a commercial scale composition of ondansetron hydrochloride dihydrate particles wherein:

(i) at least about 90% of the particles have a particle size of less than 250 µm,
(ii) at least about 40% of the particles have a particle size of greater than 60 µm, and
(iii) the particles have a mean particle size of about 50 µm to about 150 µm.

Preferably, the ondansetron hydrochloride dihydrate particles are suitable for homogeneous distribution in a tablet blend.

Preferably, the commercial scale composition has a purity of at least about 99.5% (w/w). More preferably, the commercial scale composition has a purity of at least about 99.8% (w/w). More preferably, the commercial scale composition has a purity of at least about 99.9% (w/w).

Preferably, the commercial scale composition contains about 0.05% (w/w) or less of each of 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

Preferably, the commercial scale composition contains about 0.02% (w/w) or less of 1,2,3,9-tetrahydro-9-methyl-3-methylene-4H-carbazol-4-one. Preferably, the commercial scale composition contains about 0.02% (w/w) or less of 3-[(dimethylamino)methyl]-1,2,3,9-tetrahydro-9-methyl-4H-carbazol-4-one. Preferably, the commercial scale composition contains about 0.02% (w/w) or less of methyl imidazole. Preferably, the commercial scale composition contains about 0.02% (w/w) or less of 1,2,3,9-tetrahydro-9-methyl-4H-carbazol-4-one.

Preferably, the commercial scale composition is produced as a single batch of at least about one (1) kg. More preferably, the commercial scale composition is produced as a single batch of at least about five (5) kg.

DETAILED DESCRIPTION OF THE INVENTION

Definitions

"Crystalline" refers to providing a pattern of peaks when analyzed by x-ray powder diffraction; examples of crystalline compounds include, but are not limited to, polymorphs, solvates, hydrates, and desolvated solvates; "crystallization"

refers to a process wherein a chemical compound that is dissolved or suspended in a solvent system becomes crystalline; "solvent system" refers to a solvent or mixture of solvents; "solvent" refers to a chemical compound that is a liquid at ambient temperature and pressure; "solvent for ondansetron hydrochloride" refers to a solvent in which ondansetron hydrochloride has a solubility under ambient conditions of at least about five (5) g/L; "isolating" refers to separating a chemical compound (e.g., a crystalline compound) from a reaction mixture (e.g., a solvent system); according to the present invention, an isolated compound typically has a purity of at least about 90% (w/w); "reflux temperature" refers to the temperature at which a liquid boils; "purity" refers to the percentage by weight (% w/w) of one component of a mixture; "purifying" refers to increasing the purity of a compound; "pharmaceutical grade" refers to a purity of at least about 99.0% (w/w); "crude" refers to a chemical compound that has been synthesized by a chemical reaction and isolated from the reaction mixture, but not further purified; "precipitation" refers to a process wherein a solid forms in a solution; "solution" refers to a homogeneous mixture of a solvent and a chemical compound; "suspension" refers to a heterogeneous mixture of a solvent and a chemical compound; "ambient conditions" refers to ambient temperature (i.e., about 20–25° C.) and pressure (i.e., about one (1) atmosphere); "HPLC" refers to high performance liquid chromatography; "batch size" refers to the amount of a product compound (e.g., a crystalline compound) produced during a chemical manufacturing step (e.g., a crystallization step); "composition" refers to a solid chemical compound that has been produced in a chemical manufacturing step, together with any impurities that are present with the compound; "commercial scale composition" refers to a composition that is produced as a single batch of at least about 500 grams of the composition; "precipitation medium" refers to a solvent system containing at least one nonsolvent for ondansetron hydrochloride; "nonsolvent for ondansetron hydrochloride" refers to a solvent in which ondansetron hydrochloride has a solubility under ambient conditions of less than about five (5) g/L; "water-miscible" refers to a solvent that forms a single phase when mixed with water, with no meniscus visible between layers of liquid; "suitable for homogeneous distribution in a tablet blend" refers to ondansetron hydrochloride dihydrate that is suitable for manufacturing uniform tablets containing ondansetron hydrochloride dihydrate in an amount equivalent to four (4) mg, eight (8) mg, or twenty-four (24) mg of ondansetron; "uniform tablets" refers to tablets that meet the United States Food & Drug Administration (FDA) drug content uniformity guidelines for ondansetron hydrochloride dihydrate tablets; according to these guidelines, each tablet must contain 85%–115% (w/w) of the indicated dosage, and the % relative standard deviation (% RSD) of 10 tablets must be not more than 6%.

The present invention provides a distinct and novel process for preparing ondansetron hydrochloride dihydrate having a defined particle size. The present invention provides a process for preparing ondansetron hydrochloride dihydrate particles in which at least about 70% of the particles have a particle size of less than 250 µm, comprising the steps of:

(a) preparing a solution comprising ondansetron hydrochloride and water; and (b) adding the solution into a precipitation medium which comprises a water-miscible nonsolvent for ondansetron hydrochloride, while maintaining the resulting mixture at a temperature of about 40° C. or less.

The solution in step (a) may contain any suitable amount of water. Preferably, the solution contains at least about 10% water as relative to ondansetron hydrochloride (w/w). Not wishing to be bound a theory, it is believed that this amount of water is sufficient to convert the ondansetron hydrochloride into the dihydrate crystalline form. Preferably, the solution in step (a) contains at least about 40% water (w/w).

The preparing step (a) may be performed using any suitable method. Suitable methods include, but are not limited to, methods that employ ondansetron and methods that employ ondansetron hydrochloride. For example, the step (a) may be performed by mixing ondansetron with hydrochloric acid in a solvent system that includes water. Alternatively, the step (a) may be performed by dissolving ondansetron hydrochloride in a solvent system that includes water.

Processes for preparing ondansetron are well known in the art. For example, ondansetron may be prepared by the following two steps: (a) reacting 1,2,3,9-tetrahydro-9-methyl-4H-carbazol-4-one (available from Ningbo Pharmaceutical Co. (Zhejiang Province, China)) with a paraformaldehyde reagent, and (b) reacting the resulting 1,2,3,9-tetrahydro-9-methyl-3-methylene-4H-carbazol-4-one with 2-methylimidazole to form ondansetron.

Processes for preparing ondansetron hydrochloride are also well known in the art. For example, ondansetron hydrochloride may be prepared from ondansetron by simple reaction with hydrochloric acid.

Processes for preparing ondansetron and ondansetron hydrochloride are described in detail in our copending U.S. Provisional Application Ser. No. 60/602,141 ('141 application). Other alternative methods for preparing ondansetron and ondansetron hydrochloride are also described in U.S. Pat. No. 4,695,578 ('578 patent) and U.S. Patent Application No. 2002/0115707 ('707 application). The '141 application, '578 patent, and '707 application are incorporated herein by reference in their entireties.

The ondansetron or ondansetron hydrochloride used in step (a) may be crystalline, amorphous, semisolid, syrup, a mixture thereof, or the like. Crystalline ondansetron or ondansetron hydrochloride may include polymorphs, solvates, clathrates, and the like, and mixtures thereof. Exemplary crystalline forms of ondansetron include, but are not limited to, Forms A and B, and Forms I and II (See U.S. Patent Application Nos. 2004/0019093 and 2004/0198794, each of which is incorporated herein by reference in its entirety). Exemplary crystalline forms of ondansetron hydrochloride include, but are not limited to, ondansetron hydrochloride dihydrate. Preferably, step (a) is performed by mixing crude ondansetron hydrochloride dihydrate with a solvent system comprising water.

Preferably, step (a) is performed by heating the solution to increase the solubility of the ondansetron hydrochloride in the solution sufficient to aid preparation of the solution. Preferably, step (a) is performed at a temperature of about 40° C. to about 90° C. More preferably, step (a) is performed at a temperature of about 50° C. to about 80° C. More preferably, step (a) is performed at a temperature of about 65° C. to about 70° C.

Ondansetron hydrochloride may be present in step (a) solution at a suitable concentration. Preferably, the ondansetron hydrochloride in step (a) is present at a concentration of about 100 g/L to about 1,000 g/L. More preferably, the ondansetron hydrochloride in step (a) is present at a concentration of about 200 g/L to about 500 g/L.

Step (b) involves adding the solution as prepared in step (a) into a precipitation medium to form a resulting mixture.

The precipitation medium comprises a water-miscible nonsolvent for ondansetron hydrochloride. Preferably, the water-miscible nonsolvent for ondansetron hydrochloride is a $C_2$–$C_4$ alcohol. Preferably, the $C_2$–$C_4$ alcohol is selected from the group consisting of ethanol, isopropanol, and mixtures thereof. More preferably, the $C_2$–$C_4$ alcohol is isopropanol.

Step (b) may be performed using the step (a) solution and the precipitation medium at the same or different temperatures. For example, the step (a) solution and the precipitation medium may both be at about room temperature (i.e., ambient temperature). Preferably, the step (a) solution has a temperature that is higher than the temperature of the precipitation medium during the adding step (b). Preferably, the precipitation medium has a temperature of about 30° C. or less. More preferably, the precipitation medium has a temperature of about 20° C. or less.

Step (b) is performed while maintaining the resulting mixture at a temperature of about 40° C. or less. Not wishing to be bound by theory, it is believed desirable to maintain the resulting mixture in step (b) at a suitable temperature in order to optimize the particle size of the obtained ondansetron hydrochloride dihydrate particles. For example, we have observed that an increase in temperature of the mixture may result in an increase in particle size. Without wishing to be held to any particular theory, it is believed that at elevated temperatures, the ondansetron hydrochloride may dissolve, and then crystallize as large particles as the mixture cools. Preferably, step (b) is performed while maintaining the mixture at a temperature of about 30° C. or less. More preferably, step (b) is performed while maintaining the mixture at a temperature of about 20° C. or less.

Any suitable method may be used to maintain the mixture at a suitable temperature. Suitable methods include, but are not limited to, performing step (b) in a cooling bath (e.g., ice water bath), and performing step (b) by adding the solution into the precipitation medium at a slow rate.

Not wishing to be bound by theory, it is believed that the particle size of the obtained ondansetron hydrochloride dihydrate particles is affected by the vol/vol ratio of nonsolvent for ondansetron hydrochloride to water in the mixture. Preferably, the vol/vol ratio of nonsolvent for ondansetron hydrochloride to water in the mixture is about 4:1 or greater. More preferably, the vol/vol ratio of nonsolvent for ondansetron hydrochloride to water in the mixture is about 5:1 or greater. More preferably, the vol/vol ratio of nonsolvent for ondansetron hydrochloride to water in the mixture is about 6:1 or greater. More preferably, the vol/vol ratio of nonsolvent for ondansetron hydrochloride to water in the mixture is about 7:1 or greater.

Not wishing to be bound by theory, it is further believed that the particle size of the obtained ondansetron hydrochloride is affected by the vol/vol ratio of the solution to the precipitation medium. Preferably, the solution and the precipitation medium have a vol/vol ratio of about 1:1 to about 1:10. More preferably, the solution and the precipitation medium have a vol/vol ratio of about 1:2 to about 1:5.

Optionally, the step (a) solution may include a water-miscible solvent for ondansetron hydrochloride, a water-miscible non-solvent for ondansetron hydrochloride, or both. Water miscible solvents for ondansetron hydrochloride include, but are not limited to, methanol.

Preferably, the step (a) solution includes both water and a water-miscible nonsolvent for ondansetron hydrochloride. Water-miscible nonsolvents for ondansetron hydrochloride include, but are not limited to, $C_2$–$C_4$ alcohols. $C_2$–$C_4$ alcohols include, but are not limited to, ethanol, propanol, isopropanol, and butanol. Preferably, the $C_2$–$C_4$ alcohol is selected from the group consisting of ethanol, isopropanol, and mixtures thereof. More preferably, the $C_2$–$C_4$ alcohol is isopropanol.

In accordance with the present invention, the obtained ondansetron hydrochloride dihydrate has a defined particle size. Particle size may be determined by well-known techniques, for example, see the technique set forth below (See Methodology and Protocols). Preferably, at least about 80% of the ondansetron hydrochloride dihydrate particles have a particle size of less than 250 μm. More preferably, at least about 90% of the ondansetron hydrochloride dihydrate particles have a particle size of less than 250 μm. More preferably, about 100% of the ondansetron hydrochloride dihydrate particles have a particle size of less than 250 μm.

A unique feature of the present invention is that the obtained ondansetron hydrochloride dihydrate particles have a defined particle size. Preferably, a significant amount of the particles have a particle size in the range of 60 μm to 250 μm. Preferably, at least about 30% of the ondansetron hydrochloride dihydrate particles have a particle size of greater than 60 μm. More preferably, at least about 40% of the ondansetron hydrochloride dihydrate particles have a particle size of greater than 60 μm. More preferably, at least about 50% of the ondansetron hydrochloride dihydrate particles have a particle size of greater than 60 μm. More preferably, at least about 60% of the ondansetron hydrochloride dihydrate particles have a particle size of greater than 60 μm. More preferably, at least about 70% of the ondansetron hydrochloride dihydrate particles have a particle size of greater than 60 μm. More preferably, at least about 80% of the ondansetron hydrochloride dihydrate particles have a particle size of greater than 60 μm.

Preferably, the ondansetron hydrochloride dihydrate particles have a mean particle size of about 25 μm to about 200 μm. More preferably, the ondansetron hydrochloride dihydrate particles have a mean particle size of about 40 μm to about 200 μm. More preferably, the ondansetron hydrochloride dihydrate particles have a mean particle size of about 50 μm to about 150 μm. More preferably, the ondansetron hydrochloride dihydrate particles have a mean particle size of about 60 μm to about 120 μm.

An advantage of the present invention is that the obtained ondansetron hydrochloride dihydrate particles are suitable for homogeneous distribution in a tablet blend. As such, an advantage of the present invention is that the obtained ondansetron hydrochloride dihydrate particles may be used to prepare ondansetron hydrochloride dihydrate tablets without requiring further steps to reduce particle size.

Preferably, the ondansetron hydrochloride dihydrate particles formed in step (b) of the present invention are isolated from the mixture. The particles may be isolated using any suitable method. Suitable isolation methods include, but are not limited to, filtration, decantation, and centrifugation.

Preferably, the isolated ondansetron hydrochloride dihydrate particles are dried. The isolated ondansetron hydrochloride dihydrate particles may be dried at any suitable temperature and pressure. Suitable drying conditions include, but are not limited to, ambient temperature and pressure. Preferably, the dried ondansetron hydrochloride dihydrate particles are suitable for homogeneous distribution in a tablet blend.

An advantage of the present invention is that it is not necessary to dry the isolated ondansetron hydrochloride dihydrate particles under vigorous conditions for prolonged time periods in order to obtain particles having a particle size suitable for preparing uniform ondansetron hydrochloride dihydrate tablets.

In a preferred embodiment, the present invention is suitable for the production of pharmaceutical grade ondansetron hydrochloride dihydrate from crude ondansetron hydrochloride dihydrate. Preferably, the ondansetron hydrochloride dihydrate particles have a purity of at least about 99.5% (w/w). More preferably, the ondansetron hydrochloride dihydrate particles have a purity of at least about 99.8% (w/w). More preferably, the ondansetron hydrochloride dihydrate particles have a purity of at least about 99.9% (w/w). The purity of the ondansetron hydrochloride dihydrate particles may be determined as set forth below (See Methodology and Protocols).

Preferably, the ondansetron hydrochloride dihydrate particles contain about 0.05% (w/w) or less of each individual impurity. Examples of impurities include, but are not limited to, 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

Preferably, the ondansetron hydrochloride dihydrate particles contain about 0.1% (w/w) or less of 1,2,3,9-tetrahydro-9-methyl-3-methylene-4H-carbazol-4-one. More preferably, the ondansetron hydrochloride dihydrate particles contain about 0.05% (w/w) or less of 1,2,3,9-tetrahydro-9-methyl-3-methylene-4H-carbazol-4-one. More preferably, the ondansetron hydrochloride dihydrate particles contain about 0.03% (w/w) or less of 1,2,3,9-tetrahydro-9-methyl-3-methylene-4H-carbazol-4-one. More preferably, the ondansetron hydrochloride dihydrate particles contain about 0.02% (w/w) or less of 1,2,3,9-tetrahydro-9-methyl-3-methylene-4H-carbazol-4-one. More preferably, the ondansetron hydrochloride dihydrate particles contain about 0.01% (w/w) or less of 1,2,3,9-tetrahydro-9-methyl-3-methylene-4H-carbazol-4-one.

Preferably, the ondansetron hydrochloride dihydrate particles contain about 0.1% (w/w) or less of 3-[(dimethylamino)methyl]-1,2,3,9-tetrahydro-9-methyl-4H-carbazol-4-one. More preferably, the ondansetron hydrochloride dihydrate particles contain about 0.05% (w/w) or less of 3-[(dimethylamino)methyl]-1,2,3,9-tetrahydro-9-methyl-4H-carbazol-4-one. More preferably, the ondansetron hydrochloride dihydrate particles contain about 0.03% (w/w) or less of 3-[(dimethylamino)methyl]-1,2,3,9-tetrahydro-9-methyl-4H-carbazol-4-one. More preferably, the ondansetron hydrochloride dihydrate particles contain about 0.02% (w/w) or less of 3-[(dimethylamino)methyl]-1,2,3,9-tetrahydro-9-methyl-4H-carbazol-4-one.

Preferably, the ondansetron hydrochloride dihydrate particles contain about 0.1% (w/w) or less of methyl imidazole. More preferably, the ondansetron hydrochloride dihydrate particles contain about 0.05% (w/w) or less of methyl imidazole. More preferably, the ondansetron hydrochloride dihydrate particles contain about 0.03% (w/w) or less of methyl imidazole. Preferably, the ondansetron hydrochloride dihydrate particles contain about 0.02% (w/w) or less of methyl imidazole.

Preferably, the ondansetron hydrochloride dihydrate particles contain about 0.1% (w/w) or less of 1,2,3,9-tetrahydro-9-methyl-4H-carbazol-4-one. More preferably, the ondansetron hydrochloride dihydrate particles contain about 0.05% (w/w) or less of 1,2,3,9-tetrahydro-9-methyl-4H-carbazol-4-one. More preferably, the ondansetron hydrochloride dihydrate particles contain about 0.03% (w/w) or less of 1,2,3,9-tetrahydro-9-methyl-4H-carbazol-4-one. More preferably, the ondansetron hydrochloride dihydrate particles contain about 0.02% (w/w) or less of 1,2,3,9-tetrahydro-9-methyl-4H-carbazol-4-one. More preferably, the ondansetron hydrochloride dihydrate particles contain about 0.01% (w/w) or less of 1,2,3,9-tetrahydro-9-methyl-4H-carbazol-4-one.

In another preferred embodiment, the present invention provides a process for preparing ondansetron hydrochloride dihydrate particles in which at least about 70% of the particles have a particle size of less than 250 μm, comprising the steps of:
(a) preparing a solution comprising ondansetron hydrochloride and water; and
(b) adding the solution into a precipitation medium which comprises a $C_2$–$C_4$ alcohol, while maintaining the resulting mixture at a temperature of about 40° C. or less.

In another preferred embodiment, the present invention provides a process for preparing ondansetron hydrochloride dihydrate particles in which at least about 70% of the particles have a particle size of less than 250 μm, comprising the steps of:
(a) preparing a solution comprising ondansetron hydrochloride, water, and isopropanol; and
(b) adding the solution into a precipitation medium which comprises isopropanol, while maintaining the resulting mixture at a temperature of about 30° C. or less.

In another preferred embodiment, the process of the present invention is performed at a commercial scale. Preferably, the ondansetron hydrochloride dihydrate particles are prepared as a single batch of at least about 500 grams. More preferably, the ondansetron hydrochloride dihydrate particles are prepared as a single batch of at least about one (1) kilogram. More preferably, the ondansetron hydrochloride dihydrate particles are prepared as a single batch of at least about five (5) kilograms.

In another preferred embodiment, the present invention provides a commercial scale composition of ondansetron hydrochloride dihydrate particles prepared by the process of the present invention.

In another preferred embodiment, the present invention provides a commercial scale composition of ondansetron hydrochloride dihydrate particles wherein:
(i) at least about 90% of the particles have a particle size of less than 250 μm,
(ii) at least about 40% of the particles have a particle size of greater than 60 μm, and
(iii) the particles have a mean particle size of about 50 μm to about 150 μm.

Preferably, the particles are suitable for homogeneous distribution in a tablet blend.

Preferably, the commercial scale composition has a purity of at least about 99.5% (w/w). More preferably, the commercial scale composition has a purity of at least about 99.8% (w/w). More preferably, the commercial scale composition has a purity of at least about 99.9% (w/w).

Preferably, the commercial scale composition contains about 0.05% (w/w) or less of at least one member selected from the group consisting of 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one. More preferably, the commercial scale composition contains about 0.05% (w/w) or less of each of 1,2,3,9-tetrahydro-9-methyl-3-methylene-4H-carbazol-4-one, 3-[(dimethylamino)methyl]-1,2,3,9-tetrahydro-9-methyl- 4H-carbazol-4-one, methyl imidazole, and 1,2,3,9-tetrahydro-9-methyl-4H-carbazol-4-one.

Preferably, the commercial scale composition contains about 0.03% (w/w) or less of at least one member selected from the group consisting of 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one. More preferably, the commercial scale composition contains about 0.03% (w/w) or less of each of 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

Preferably, the commercial scale composition contains about 0.02% (w/w) or less of at least one member selected from the group consisting of 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one. More preferably, the commercial scale composition contains about 0.02% (w/w) or less of each of 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

As stated above, "composition" refers to a solid chemical compound that has been produced in a chemical manufacturing step, together with any impurities that are present with the compound. Impurities are intended to include, but are not limited to, undesired side-products formed during chemical synthesis. Examples of impurities include, but are not limited to, 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

As stated above, "commercial scale composition" refers to a composition that is produced as a single batch of at least about 500 grams of the composition. Preferably, the commercial scale composition is produced as a single batch of at least about one (1) kg. More preferably, the commercial scale composition is produced as a single batch of at least about five (5) kg.

According to the invention, commercial scale compositions include, but are not limited to, commercial scale compositions that have not been subjected to HPLC (high pressure liquid chromatography) purification, commercial scale compositions that have not been subjected to recrystallization, and commercial scale compositions that have not been subjected to any purification procedure.

Methodology and Protocols

Particle Size Determination by Laser Diffraction

| Instrument | MALVERN Mastersizer 2000, Particle Size Analyzer (or equivalent) |
|---|---|
| Technical | Small Volume Module - Hydro 2000S |
| Data | Range            0.02 µm to 2,000 µm |
| | Pump/Stirrer Speed   2,000 RPM |
| | Ultrasound            10% |
| Dispersant | Hexane (degassed) |
| Surfactant | SPAN ® 85 |
| Background | Small Volume Module filled with Dispersant plus five (5) drops of Surfactant |
| Sample | About fifty (50) mg of ondansetron hydrochloride dihydrate particles to be analyzed in about twenty-five (25) mL of Dispersant plus two (2) drops of Surfactant |
| Obscuration | About twelve (12) percent (%) |

Purity Determination by HPLC

Purity was determined using a high performance liquid chromatography (HPLC) instrument with a variable wavelength detector.

(a) Chromatographic Conditions

| Column | Merck Lichrospher 100 CN, 250 × 4.6 mm, 5 µm (or equivalent) |
|---|---|
| Flow Rate | 1.0 mL/min |
| Column temperature | Ambient |
| Detection | UV at 216 nm |
| Injection volume | 20 µL |
| Run time | 15 min for Standard solutions and Known Impurities Resolution solution |
| | 40 min for Sample solution |
| Diluent | Mobile phase |

(b) Mobile Phase

Monobasic potassium phosphate ($KH_2PO_4$, 6.8 g) was dissolved in 1,000 mL water in a 1,000-mL flask. The resulting buffer solution (800 mL) was mixed with acetonitrile (200 mL). The pH of the resulting mixture was adjusted to 4.0 with 85% phosphoric acid to provide the mobile phase.

(c) Known Impurities Resolution Solution

The following known impurities were used: 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

Each known impurity (about five (5) mg) was added to a separate 50-mL volumetric flask. To each flask was added acetonitrile (about five (5) mL) and diluent (about 20 mL), and the solutions were sonicated to ensure complete dissolution. Each flask was then filled to volume with diluent.

In the same way, ondansetron hydrochloride dihydrate (about fifty (50) mg) was added to a separate 50-mL volumetric flask. To the flask was added acetonitrile (about five (5) mL) and diluent (about 20 mL), and the solution was sonicated to ensure complete dissolution. The flask was then filled to volume with diluent.

An aliquot (five (5) mL) of each prepared known impurity solution was added to a single 50-mL volumetric flask, and the flask was filled to volume with diluent. A 2.5-mL aliquot of the resulting solution was added to a 50-mL volumetric flask. To the same flask was added a 2.5 mL aliquot of the prepared ondansetron hydrochloride dihydrate solution, and the flask was then diluted to volume with diluent to provide the Known Impurities Resolution Solution.

(d) Ondansetron Hydrochloride Dihydrate Sample Solution Approximately fifty (50) mg of the ondansetron hydrochloride dihydrate sample to be assayed, accurately weighed, was transferred into a 50-mL volumetric flask. To the flask was added acetonitrile (about five (5) mL) and diluent (about 20 mL), and the solution was sonicated to ensure complete dissolution. The flask was then filled to volume with diluent.

A 2.5-mL aliquot of the resulting solution was added to a 50-mL volumetric flask, and the flask was diluted to volume with diluent to provide the Ondansetron Hydrochloride Dihydrate Sample Solution.

(e) Ondansetron Hydrochloride Dihydrate Standard Solution

Approximately fifty (50) mg of ondansetron hydrochloride dihydrate, accurately weighed, was transferred into a 50-mL volumetric flask. To the flask was added acetonitrile (about five (5) mL) and diluent (about 20 mL), and the solution was sonicated to ensure complete dissolution. The flask was then filled to volume with diluent.

A 2.5-mL aliquot of the resulting solution was added to a 50-mL volumetric flask, and the flask was diluted to volume with diluent to provide the Ondansetron Hydrochloride Dihydrate Standard Solution.

(f) Standard Solution for Determination of Known Impurities

A 2.5-mL aliquot of the ondansetron hydrochloride dihydrate standard solution was added to 25-mL volumetric flask, and the flask was filled to volume with diluent. A 2.5-mL aliquot of the resulting solution was then added to a 50-mL volumetric flask, and the flask was filled to volume with diluent to provide the Standard Solution for Determination of Known Impurities.

Each of the standard and sample solutions was stable for three (3) days when stored at ambient temperature.

(g) HPLC Protocol

The Known Impurities Resolution Solution, six (6) replicate injections of the Standard Solution for Determination of Known Impurities, and five (5) replicate injections of the Ondansetron Hydrochloride Dihydrate Standard Solution were made.

Resolution factors were calculated according to the United States Pharmacopeia (USP) <621>. The resolution factor between ondansetron and 3-[(dimethylamino)methyl]-1,2,3,9-tetrahydro-9-methyl-4H-carbazol-4-one was not less than 2.0.

The relative standard deviation of five (5) replicate injections of the ondansetron hydrochloride dihydrate standard solution was not more than 2.0%. The relative standard deviation of six (6) replicate injections of the standard solution for determination of known impurities was not more than 10.0%. If necessary, the mobile phase composition and/or flow rate were adjusted to meet the chromatographic parameters.

Typical chromatographic parameters are listed in the following table:

The limit of detection is the minimum concentration at which the analyte can reliably be detected. The limit of quantitation is the minimum concentration at which the analyte can reliably be quantified. Limits of detection and quantitation were determined by comparing measured signals from samples with known low concentrations of analyte to measured signals from blank samples. The relative response factor is the ratio of slopes provided by calibration curves for analyte and corresponding internal standard (or surrogate and corresponding internal standard). The resolution is the separation of two peaks in terms of their average peak width at base ($t_{R2} > t_{R1}$):

$$\text{Resolution} = \frac{(t_{R2} - t_{R1})}{(w_{b1} + w_{b2})/2} = \frac{2(t_{R2} - t_{R1})}{(w_{b1} + w_{b2})}$$

In the case of two adjacent peaks it may be assumed that $W_{b1} = W_{b2}$, and thus, the width of the second peak may be substituted for the average value: Resolution=$(t_{R2} - t_{R1})/W_{b2}$.

(h) Calculation of Assay $$\% \text{ Assay (calculated on dried basis)} = \frac{Wst \times Ssm \times Ast \times 100}{Sst \times Wsm \times (100 - Msm)}$$

Wst=Weight of standard in mg
Wsm=Weight of sample in mg
Ssm=Peak area of ondansetron obtained from sample solution
Sst=Average peak area of ondansetron obtained from ondansetron hydrochloride dihydrate standard solution
Ast=Assay of ondansetron standard in percent
Msm=Moisture content in sample in percent (i) Calculation of Purity $$\% \text{ Purity} = 100 - (\% \text{ known impurities} + \% \text{ unknown impurities})$$

$$\% \text{ known or unknown impurity} = \frac{Wst \times Ssm \times Ast}{Sst \times Wsm \times RRF \times 200}$$

| Compound | Retention Time (min) | Relative Retention Time | Limit of Detection (LOD) | Limit of Quantitation (LOQ) | Relative Response Factor | Resolution |
|---|---|---|---|---|---|---|
| Methyl imidazole | 2.5 | 0.30 | 0.02% | 0.03% | 0.6 | — |
| 3-[(dimethylamino)methyl]-1,2,3,9-tetrahydro-9-methyl-4H-carbazol-4-one | 6.9 | 0.84 | 0.01% | 0.03% | 1.0 | 23.1 |
| Ondansetron | 8.3 | 1.00 | 0.01% | 0.03% | 1.0 | 4.8 |
| 1,2,3,9-tetrahydro-9-methyl-4H-carbazol-4-one | 10.6 | 1.27 | 0.01% | 0.03% | 1.4 | 6.4 |
| 1,2,3,9-tetrahydro-9-methyl-3-methylene-4H-carbazol-4-one | 13.7 | 1.65 | 0.01% | 0.03% | 1.5 | 7.3 |

Wst=Weight of standard in mg
Wsm=Weight of sample in mg
Ssm=Peak area of impurity obtained from sample solution
Sst=Average peak area of ondansetron obtained from ondansetron hydrochloride dihydrate standard solution
Ast=Assay of ondansetron standard in percent
RRF=Relative Response Factor (1.0 for unknown impurities)

Tablet Drug Content Determination by HPLC

Tablet content of ondansetron hydrochloride dihydrate was determined using a high performance liquid chromatography (HPLC) instrument with a variable wavelength detector.

(a) Chromatographic Conditions

| Column | Merck Lichrospher 100 CN, 250 × 4.0 mm, 5 µm (or equivalent) |
|---|---|
| Flow Rate | 1.0 mL/min |
| Column temperature | 30° C. |
| Detection | UV at 216 nm |
| Injection volume | 20 µL |
| Run time | 15 min for Standard solutions and Known Impurities Resolution solution |
|  | 40 min for Sample solution |
| Diluent | Mobile phase |
| Needle wash | Water:acetonitrile (20:80) |

(b) Mobile Phase

Monobasic potassium phosphate ($KH_2PO_4$, 6.8 g) was dissolved in 1,000 mL water in a 1,000-mL flask. The resulting buffer solution (800 mL) was mixed with acetonitrile (200 mL). The pH of the resulting mixture was adjusted to 4.0 with 85% phosphoric acid to provide the mobile phase.

(c) Ondansetron Hydrochloride Dihydrate Stock Solution

Approximately 25 mg of ondansetron hydrochloride dihydrate, accurately weighed, was transferred into a 50-mL volumetric flask. To the flask was added diluent (about 30 mL), and the solution was sonicated to ensure complete dissolution. The flask was then filled to volume with diluent to provide the Ondansetron Hydrochloride Dihydrate Stock Solution.

(d) Ondansetron Hydrochloride Dihydrate Standard Solution

A five (5) mL aliquot of the Ondansetron Hydrochloride Dihydrate Stock Solution was added to a 50-mL volumetric flask, and the flask was diluted to volume with diluent to provide the Ondansetron Hydrochloride Dihydrate Standard Solution.

(e) Standard Solution for Determination of Known Impurities

A 2.5-mL aliquot of the Ondansetron Hydrochloride Dihydrate Standard Solution was added to 25-mL volumetric flask, and the flask was filled to volume with diluent. A 2.5-mL aliquot of the resulting solution was then added to a 50-mL volumetric flask, and the flask was filled to volume with diluent to provide the Standard Solution for Determination of Known Impurities.

(f) Known Impurities Stock Solution

The following known impurities were used: 1,2,3,9-tetrahydro-9-methyl-3-methylene-4H-carbazol-4-one, 3-[(dimethylamino)methyl]-1,2,3,9-tetrahydro-9-methyl-4H-carbazol-4-one, methyl imidazole, and 1,2,3,9-tetrahydro-9-methyl-4H-carbazol-4-one.

Each known impurity (about ten (10) mg) was added to a separate 20-mL volumetric flask. To each flask was added acetonitrile (about fifteen (15) mL), and the solutions were sonicated to ensure complete dissolution. Each flask was then filled to volume with acetonitrile.

A 2.0 mL aliquot from each of the resulting solution was transferred into a single 100-mL volumetric flask. The flask was then filled to volume with acetonitrile to provide the Known Impurities Stock Solution.

(g) Known Impurities Resolution Solution

A 2.5 mL aliquot of the Known Impurities Stock Solution and a five (5) mL aliquot of the Ondansetron Hydrochloride Dihydrate Stock Solution were combined in a 50-mL volumetric flask. The flask was then filled to volume with diluent to provide the Known Impurities Resolution Solution.

(h) Ondansetron Hydrochloride Dihydrate Tablet Sample Solution—Four (4) mg Tablets A four (4) mg tablet was transferred into a 100-mL volumetric flask, and the flask was filled to about 70% of the volume with Diluent. The resulting mixture was shaken for fifteen (15) minutes and then sonicated for ten (10) minutes. The flask was then filled to volume with Diluent to provide the Ondansetron Hydrochloride Dihydrate Tablet Sample Solution for Four (4) mg Tablets.

(i) Ondansetron Hydrochloride Dihydrate Tablet Sample Solution—Eight (8) mg Tablets An eight (8) mg tablet was transferred into a 20-mL volumetric flask, and the flask was filled to about 70% of the volume with Diluent. The resulting mixture was shaken for fifteen (15) minutes and then sonicated for ten (10) minutes. The flask was then filled to volume with Diluent.

A five (5) mL aliquot of the resulting solution was transferred to a closed centrifuge tube. The tube was then centrifuged at about 4,000 RPM for ten (10) minutes. The supernatant was transferred to a 50-mL volumetric flask. The flask was filled to volume with Diluent to provide the Ondansetron Hydrochloride Dihydrate Tablet Sample Solution for Eight (8) mg Tablets.

(j) Ondansetron Hydrochloride Dihydrate Tablet Sample Solution—24 mg Tablets

A 24 mg tablet was transferred into a 25-mL volumetric flask, and the flask was filled to about 70% of the volume with Diluent. The resulting mixture was shaken for fifteen (15) minutes, then sonicated for ten (10) minutes. The flask was then filled to volume with Diluent.

A two (2) mL aliquot of the resulting solution was transferred to a closed centrifuge tube. The tube was then centrifuged at about 4,000 RPM for ten (10) minutes. The supernatant was transferred to a 50-mL volumetric flask. The flask was filled to volume with Diluent to provide the Ondansetron Hydrochloride Dihydrate Tablet Sample Solution for 24 mg Tablets.

(k) HPLC Protocol The Known Impurities Resolution Solution was injected. Resolution factors were calculated according to the United States Pharmacopeia (USP) <621>. The resolution factor between ondansetron and 3-[(dimethylamino)methyl]-1,2,3,9-tetrahydro-9-methyl-4H-carbazol-4-one was not less than 2.0. The resolution factor between ondansetron and 1,2,3,9-tetrahydro-9-methyl-4H-carbazol-4-one was not less than 2.0.

The relative standard deviation of five (5) replicate injections of the Ondansetron Hydrochloride Dihydrate Standard Solution was not more than 2.0%. The relative standard deviation of six (6) replicate injections of the Standard Solution for Determination of Known Impurities was not more than 10.0%. If necessary, the mobile phase composition and/or flow rate were adjusted to meet the chromatographic parameters.

Typical chromatographic parameters are listed in the following table:

| Compound | Retention Time (min) | Relative Retention Time | Limit of Detection (LOD) | Limit of Quantitation (LOQ) | Relative Response Factor | Resolution |
|---|---|---|---|---|---|---|
| Methyl imidazole | 2.7 | 0.30 | 0.02% | 0.03% | 0.54 | — |
| 3-[(dimethyl-amino)methyl]-1,2,3,9-tetrahydro-9-methyl-4H-carbazol-4-one | 7.4 | 0.84 | 0.01% | 0.03% | 0.91 | 19 |
| Ondansetron | 8.8 | 1.00 | 0.01% | 0.03% | 1.0 | 3.8 |
| 1,2,3,9-tetrahydro-9-methyl-4H-carbazol-4-one | 10.4 | 1.19 | 0.01% | 0.03% | 1.24 | 4.0 |
| 1,2,3,9-tetrahydro-9-methyl-3-methylene-4H-carbazol-4-one | 13.3 | 1.52 | 0.01% | 0.03% | 1.31 | 6.7 |

(l) Calculation of Assay $$\text{Assay (\% label claim)} = \frac{Wst \times Ssm \times Vsm \times Dsm \times Ast \times F}{Sst \times Vst \times Dst \times LP}$$

Wst=Weight of ondansetron hydrochloride dihydrate standard in mg
Ssm=Peak area of ondansetron obtained from tablet sample solution
Sst=Average peak area of ondansetron obtained from ondansetron hydrochloride dihydrate standard solution
Vsm=Initial volume of tablet sample solution preparation in mL
Vst=Initial volume of ondansetron hydrochloride dihydrate standard solution preparation in mL
Dsm=Dilution factor of tablet sample solution preparation
Dst=Dilution factor of ondansetron hydrochloride dihydrate standard solution preparation
F=0.889 (molecular weight ratio between ondansetron and ondansetron hydrochloride)
LP=Label Potency
Ast=Potency of ondansetron hydrochloride dihydrate standard in percent The present invention provides a method of preparing ondansetron hydrochloride dihydrate particles suitable for homogeneous distribution in a tablet blend. The method is simple, rapid, high-yielding, and suited for industrial use.

The invention is further illustrated, but not limited, by the following examples.

EXAMPLES

Example 1

Commercial Scale Preparation of Ondansetron Hydrochloride Dihydrate Particles

Crude ondansetron hydrochloride dihydrate (5.5 kg, 15.1 mol) and water (10 L) were added to a first vessel containing isopropanol (10 L). The mixture was heated to 60° C.–70° C. until the ondansetron hydrochloride dihydrate was completely dissolved.

Isopropanol (47 L) was added to a second vessel, and the temperature was maintained at not more than 20° C. (i.e., about 15° C.).

The hot solution of ondansetron hydrochloride dihydrate was transferred slowly into the second vessel over the course of about 5–10 minutes, while maintaining the temperature of the resulting mixture at not more than 35° C. (i.e., about 25° C.). After the addition, the mixture was cooled to about 20° C. and stirred for about one hour.

The resulting precipitate was filtered, washed with isopropanol (10 L), and dried under a nitrogen atmosphere ($N_2$ flow about 20 L/min, $N_2$ pressure about 1 bar) at 35° C.–40° C. for about 6 hours to provide ondansetron hydrochloride dihydrate particles (5.43 kg; 99% yield).

The particle size of the obtained ondansetron hydrochloride dihydrate particles was determined as set forth above (See Methodology and Protocols). The mean particle size and particle size distribution of the particles (fraction of particles by volume smaller than specified diameter) are presented in the following table.

| Mean | <60 μm | <150 μm | <250 μm |
|---|---|---|---|
| 96 μm | 19% | 90% | 100% |

Example 2

Commercial Scale Preparation of Ondansetron Hydrochloride Dihydrate Particles

A commercial scale batch of ondansetron hydrochloride dihydrate particles was prepared using a procedure analogous to the procedure set forth in Example 1. In particular, crude ondansetron hydrochloride dihydrate (5.9 kg, 16.2 mol) and water (8.3 L) were added to a first vessel containing isopropanol (8.3 L). The mixture was heated to 65° C.–75° C. until the ondansetron hydrochloride dihydrate was completely dissolved.

Isopropanol (42 L) was added to a second vessel, and the temperature was maintained at not more than 20° C.

The hot solution of ondansetron hydrochloride dihydrate was transferred slowly into the second vessel over the course of about 20 minutes, while maintaining the temperature of the resulting mixture at not more than 35° C. After the addition, the mixture was cooled to about 20° C. and stirred for about one hour.

The resulting precipitate was filtered, washed with isopropanol, and dried in a rotary evaporator at 35° C. and 60 mbar. The yield of ondansetron hydrochloride dihydrate particles was 91%.

The particle size was measured as in Example 1. The results are presented in the following table.

| Mean | <63 μm | <150 μm | <250 μm |
|---|---|---|---|
| 81 μm | 31% | 90% | 100% |

Example 3

Commercial Scale Preparation of Ondansetron Hydrochloride Dihydrate Particles

A commercial scale batch of ondansetron hydrochloride dihydrate particles was prepared using a procedure analogous to the procedure set forth in Example 1. In particular, ondansetron hydrochloride dihydrate prepared in Example 2 (4.9 kg, 13.4 mol) and water (8.3 L) were added to a first vessel containing isopropanol (8.3 L). The mixture was heated to 65° C.–75° C. until the ondansetron hydrochloride dihydrate was completely dissolved.

Isopropanol (42 L) was added to a second vessel, and the temperature was maintained at not more than 20° C.

The hot solution of ondansetron hydrochloride dihydrate was transferred slowly into the second vessel over the course of about 20 minutes, while maintaining the temperature of the resulting mixture at not more than 35° C. After the addition, the mixture was cooled to about 20° C. and stirred for about one hour.

The resulting precipitate was filtered, washed with isopropanol, and dried at not more than 40° C. The yield of ondansetron hydrochloride dihydrate particles was 89%.

The particle size was measured as in Example 1. The results are presented in the following table.

| Mean | <63 μm | <150 μm | <250 μm |
|---|---|---|---|
| 81 μm | 34% | 85% | 100% |

Example 4

Commercial Scale Preparation of Ondansetron Hydrochloride Dihydrate Particles

A commercial scale batch of ondansetron hydrochloride dihydrate particles was prepared using a procedure analogous to the procedure set forth in Example 1. In particular, ondansetron hydrochloride dihydrate (3.98 kg, 10.88 mol) and water (7.0 L) were added to a first vessel containing isopropanol (7.0 L). The mixture was heated to 65° C.–75° C. until the ondansetron hydrochloride dihydrate was completely dissolved.

Isopropanol (34 L) was added to a second vessel, and the temperature was maintained at not more than 20° C.

The hot solution of ondansetron hydrochloride dihydrate was transferred slowly into the second vessel over the course of about 20 minutes, while maintaining the temperature of the resulting mixture at not more than 35° C. After the addition, the mixture was cooled to about 20° C. and stirred for about one hour.

The resulting precipitate was filtered, washed with isopropanol, and dried at not more than 40° C. The yield of ondansetron hydrochloride dihydrate particles was 89%.

The particle size was measured as in Example 1. The results are presented in the following table.

| Mean | <63 μm | <150 μm | <250 μm |
|---|---|---|---|
| 81 μm | 12% | 85% | 100% |

Example 5

Preparation of Ondansetron Hydrochloride Dihydrate Particles

Ondansetron hydrochloride dihydrate particles were prepared using a procedure analogous to the procedure set forth in Example 1. In particular, ondansetron hydrochloride dihydrate (20 grams, 5.5 mmol) and water (20 mL) were added to a first vessel containing isopropanol (20 mL). The mixture was heated to 65° C.–75° C. until the ondansetron hydrochloride dihydrate was completely dissolved.

Isopropanol (100 mL) was added to a second vessel, and the temperature was maintained at not more than 20° C.

The hot solution of ondansetron hydrochloride dihydrate was transferred slowly into the second vessel over the course of about five (5) minutes, while maintaining the temperature of the resulting mixture at not more than 35° C. After the addition, the mixture was cooled to about 20° C. and stirred for about one hour.

The resulting precipitate was filtered, washed with isopropanol, and dried at not more than 40° C. The yield of ondansetron hydrochloride dihydrate particles was 90%.

The particle size was measured as in Example 1. The results are presented in the following table.

| Mean | <63 μm | <150 μm | <250 μm |
|---|---|---|---|
| 89 μm | 26% | 85% | 100% |

Example 6

Preparation of Ondansetron Hydrochloride Dihydrate Particles Using Solution that Does Not Contain Isopropanol Ondansetron hydrochloride dihydrate (100 g, 274 mmol) was dissolved in water (140 mL) in a first vessel. The mixture was heated to 65° C.–70° C. until the ondansetron hydrochloride dihydrate was completely dissolved.

Isopropanol (700 mL) was added to a second vessel at a temperature of 20° C.

The hot solution of ondansetron hydrochloride dihydrate was transferred slowly into the second vessel over the course of about 10–15 minutes, while maintaining the temperature of the resulting mixture at not more than 30° C. After the addition, the mixture was cooled to 16° C. and stirred for about one hour.

The resulting precipitate was filtered and washed with isopropanol. The particle size of the obtained wet ondansetron hydrochloride dihydrate particles was measured without drying (i.e., immediately after filtration). In addition, the particle size of four samples of the wet ondansetron hydrochloride dihydrate particles was measured after drying under varying conditions: (a) six (6) hours drying under ambient conditions, (b) two (2) hours drying at 40° C., (c) four (4) hours drying at 40° C., and (d) eight (8) hours drying at 40° C., followed by two (2) days at 25° C. The particle size was determined as in Example 1. The results are presented in the following table.

| Drying Conditions | <60 μm | <280 μm | <290 μm | <350 μm |
|---|---|---|---|---|
| None (i.e., wet particles after filtration) | 31% | 100% | | |
| Ambient conditions, six (6) hours | 28% | 100% | | |
| 40° C., two (2) hours | 35% | | 100% | |
| 40° C., four (4) hours | 28% | 100% | | |
| 40° C., eight (8) hours; 25° C., two (2) days | 15% | | | 100% |

This Example demonstrates that the particle size of the ondansetron hydrochloride dihydrate particles of the present invention remains substantially unchanged before and after drying. Thus, it is not necessary to perform an additional particle size reduction step (e.g., grinding, sieving, prolonged drying under vigorous conditions, etc.) before formulating the particles into ondansetron hydrochloride dihydrate tablets.

Example 7

Purity Determination

The purity of the ondansetron hydrochloride dihydrate particles prepared in Examples 1 and 4 was determined using HPLC as set forth above (See Methodology and Protocols). The quantities of known and unknown impurities are presented in the following table:

| Compound | Example 1 | Example 4 |
|---|---|---|
| 1,2,3,9-tetrahydro-9-methyl-3-methylene-4H-carbazol-4-one | 0.03% | <0.01% |
| 3-[(dimethylamino)methyl]-1,2,3,9-tetrahydro-9-methyl-4H-carbazol-4-one | <0.02% | 0.03% |
| Methyl imidazole | <0.02% | <0.02% |
| 1,2,3,9-tetrahydro-9-methyl-4H-carbazol-4-one | <0.02% | <0.01% |
| Individual unknown (RRT 0.51) | 0.04% | <0.01% |
| Individual unknown (RRT 0.54) | <0.03% | <0.01% |
| Individual unknown (RRT 0.78) | <0.03% | <0.01% |
| Individual unknown (RRT 0.89) | 0.05% | <0.03% |
| Total | 0.1% | 0.03% |

The purity of the ondansetron hydrochloride particles prepared in Example 1 was 99.9%. The purity of the ondansetron hydrochloride particles prepared in Example 4 was >99.9%. Thus, it is not necessary to perform an additional purification step before formulating the particles into ondansetron hydrochloride dihydrate tablets.

Example 8

Tablets Containing Ondansetron Hydrochloride Dihydrate Particles

The ondansetron hydrochloride dihydrate particles prepared in Example 4 were homogeneously distributed in three separate batches of conventional tableting excipients. The first batch (two (2) kilograms (kg)) was formulated into 125 mg tablets containing the equivalent of four (4) milligrams (mg) ondansetron free base (i.e., about five (5) mg of ondansetron hydrochloride dihydrate). The second batch (1.5 kg) was formulated into 250 mg tablets containing the equivalent of eight (8) mg ondansetron free base (i.e., about ten (10) mg of ondansetron hydrochloride dihydrate). The third batch (two (2) kg) was formulated into 270 mg tablets containing the equivalent of twenty-four (24) mg ondansetron free base (i.e., about thirty (30) mg of ondansetron hydrochloride dihydrate).

Ten (10) tablets from each batch were assayed for ondansetron content using an HPLC procedure as set forth above (See Methodology and Protocols). The results are presented below.

Four (4) mg Tablets
　Individual assays (%): 103.02, 98.85, 104.73, 100.44, 102.84, 99.45, 97.94, 102.26, 101.21, 100.47
　Average: 101.1%, RSD=2.1%

Eight (8) mg Tablets
　Individual assays (%): 100.73, 100.56, 99.96, 99.87, 99.50, 101.26, 102.56, 99.25, 100.65, 99.39
　Average: 100.4%, RSD=1.0%

Twenty-four (24) mg Tablets
　Individual assays (%): 100.55, 98.88, 98.77, 105.23, 100.66, 103.71, 100.78, 102.02, 101.63, 102.42
　Average: 101.5%; RSD=2.0%

Each batch of tablets met the United States Food & Drug Administration (FDA) uniformity guidelines for ondansetron dihydrate tablets. As such, this Example demonstrates that the ondansetron hydrochloride dihydrate particles were suitable for homogeneous distribution in a tablet blend.

Numerous references, including patents, patent applications and various publications, are cited and discussed in the description of this invention. All references cited and discussed in this specification are incorporated herein by reference in their entirety and to the same extent as if each reference was individually incorporated by reference.

What is claimed is:

1. A process for preparing ondansetron hydrochloride dihydrate particles in which at least about 70% of the particles have a particle size of less than 250 μm, comprising the steps of:
　(a) preparing a solution comprising ondansetron hydrochloride and water;
　(b) adding the solution into a precipitation medium which comprises a $C_2$–$C_4$ alcohol;
　(c) stirring the resulting mixture and maintaining the resulting mixture at a temperature of about 40° C. or less; and
　(d) obtaining ondansetron hydrochloride in the solid state, wherein the duration of step (c) is less than or equal to about 1 hour.

2. The process of claim 1, wherein step (a) is performed at a temperature of about 40° C. to about 90° C.

3. The process of claim 1, wherein step (a) is performed at a temperature of about 50° C. to about 80° C.

4. The process of claim 1, wherein step (a) is performed at a temperature of about 65° C. to about 70° C.

5. The process of claim 1, wherein the precipitation medium has a temperature of about 30° C. or less.

6. The process of claim 1, wherein the precipitation medium has a temperature of about 20° C. or less.

7. The process of claim 1, wherein the $C_2$–$C_4$ alcohol in the precipitation medium is isopropanol.

8. The process of claim 1, wherein step (a) is performed by mixing ondansetron with hydrochloric acid in a solvent system comprising water.

9. The process of claim 1, wherein the ondansetron hydrochloride in step (a) is present at a concentration of about 100 g/L to about 1,000 g/L.

10. The process of claim 1, wherein the ondansetron hydrochloride in step (a) is present at a concentration of about 200 g/L to about 500 g/L.

11. The process of claim 1, wherein the solution and the precipitation medium have a vol/vol ratio of about 1:1 to about 1:10.

12. The process of claim 1, wherein the solution and the precipitation medium have a vol/vol ratio of about 1:2 to about 1:5.

13. The process of claim 1, wherein the solution further comprises a $C_2$–$C_4$ alcohol.

14. The process of claim 1, wherein the solution further comprises isopropanol.

15. The process of claim 1, wherein at least about 80% of the ondansetron hydrochloride dihydrate particles have a particle size of less than 250 µm.

16. The process of claim 1, wherein at least about 90% of the ondansetron hydrochloride dihydrate particles have a particle size of less than 250 µm.

17. The process of claim 1, wherein at least about 30% of the ondansetron hydrochloride dihydrate particles have a particle size of greater than 60 µm.

18. The process of claim 1, wherein at least about 60% of the ondansetron hydrochloride dihydrate particles have a particle size of greater than 60 µm.

19. The process of claim 1, wherein the ondansetron hydrochloride dihydrate particles have a mean particle size of about 25 µm to about 200 µm.

20. The process of claim 1, wherein the ondansetron hydrochloride dihydrate particles have a mean particle size of about 50 µm to about 150 µm.

21. The process of claim 1, wherein the ondansetron hydrochloride dihydrate particles are suitable for homogeneous distribution in a tablet blend.

22. A process for preparing ondansetron hydrochloride dihydrate particles in which at least about 70% of the particles have a particle size of less than 250 µm, comprising the steps of:

(a) preparing a solution comprising ondansetron hydrochloride, water, and isopropanol; and (b) adding the solution into a precipitation medium which comprises isopropanol, while maintaining the resulting mixture at a temperature in the range of from about 16° C. to about 30° C.

23. The process of claim 22, wherein the isopropanol and the water are present in the resulting mixture at a vol/vol ratio of about 5:1 or greater.

24. The process of claim 1, wherein step (a) comprises preparing a solution consisting of ondansetron hydrochloride and water.

25. The process of claim 1, wherein in step (c) the resulting mixture is maintained at a temperature in the range of from about 16° C. to about 40° C.

26. The process of claim 1, wherein the isopropanol and the water are present in the resulting mixture at a vol/vol ratio in the range of from about 4:1 to about 6:1.

* * * * *